United States Patent
Zhou et al.

(10) Patent No.: US 11,547,671 B2
(45) Date of Patent: Jan. 10, 2023

(54) GEL PRODUCT INSTANT-DISSOLVING BLOCK AND PREPARATION METHOD THEREOF

(71) Applicant: DONG-E E-JIAO CO., LTD, Liaocheng (CN)

(72) Inventors: Xiangshan Zhou, Liaocheng (CN); Yan Zhang, Liaocheng (CN); Yangen Sun, Liaocheng (CN); Yufeng Qin, Liaocheng (CN); Yucui Jin, Liaocheng (CN); Chunyan Wang, Liaocheng (CN); Li Li, Liaocheng (CN); Lu Zhang, Liaocheng (CN); Xuelong Yu, Liaocheng (CN)

(73) Assignee: DONG-E E-JIAO CO., LTD, Liaocheng (CN)

( * ) Notice: Subject to any disclaimer, the term of this patent is extended or adjusted under 35 U.S.C. 154(b) by 24 days.

(21) Appl. No.: 16/963,846

(22) PCT Filed: May 31, 2018

(86) PCT No.: PCT/CN2018/000201
§ 371 (c)(1),
(2) Date: Jul. 22, 2020

(87) PCT Pub. No.: WO2019/148307
PCT Pub. Date: Aug. 8, 2019

(65) Prior Publication Data
US 2020/0397707 A1    Dec. 24, 2020

(30) Foreign Application Priority Data
Jan. 30, 2018 (CN) .......................... 201810088477.8

(51) Int. Cl.
*A61K 9/20* (2006.01)
*A61K 9/00* (2006.01)
*A61K 35/36* (2015.01)

(52) U.S. Cl.
CPC .......... *A61K 9/2095* (2013.01); *A61K 9/2063* (2013.01); *A61K 35/36* (2013.01); *A61K 9/0056* (2013.01)

(58) Field of Classification Search
CPC .... A61K 9/2095; A61K 9/2063; A61K 35/36; A61K 9/0056
USPC ........................................................ 424/465
See application file for complete search history.

(56) References Cited

FOREIGN PATENT DOCUMENTS

| CN | 1079148 A | 12/1993 |
|---|---|---|
| CN | 1093577 A | 10/1994 |
| CN | 101912419 A | 12/2010 |
| CN | 107281246 A | 10/2017 |
| CN | 107440053 A | 12/2017 |

OTHER PUBLICATIONS

Kim et.al. (Vacuum-Belt Drying of Rabbiteye Blueberry (*Vaccinium ashei*) Slurries: Influence of Drying Conditions on Physical and Quality Properties of Blueberry Powder, Food Bioprocess Technol, 6:3227-3237), (Year: 2013).*
Liu et.al. (Mathematical modeling for thin layer vacuum belt dryingofPanax notoginsengextract, Energy Conversion and Management 50, pp. 928-932). (Year: 2009).*
Rui-Juan Mao et al., Preparation of instant Colla Corii Asini granule by vacuity and microwave drying, Food Science and Technology, 2013, pp. 98-101, vol. 38 No. 10.

* cited by examiner

*Primary Examiner* — Adam C Milligan
(74) *Attorney, Agent, or Firm* — Bayramoglu Law Offices LLC

(57) ABSTRACT

A method for preparing a gel product instant-dissolving block includes: adding water into a raw material to dissolve the raw material and carrying out concentrating to obtain a gel solution; carrying out a drying treatment on the gel solution to obtain an irregular cellular gel body; grinding the gel body and carrying out screening to obtain gel powder with a particle size being equal to or larger than 80 meshes; moistening the gel powder with 85 to 95% alcohol and carrying out compression at a compression ratio of 30% to 60% to obtain a block, thereby obtaining the gel product instant-dissolving block. The gel product instant-dissolving block of the present invention has a loose pore structure at the inside, has a high superficial area/volume ratio and has a product density of 0.4 to 0.8 g/cm$^3$, and is capable of being rapidly dissolved within 2 minutes in hot water.

12 Claims, 2 Drawing Sheets

GEL PRODUCT INSTANT-DISSOLVING BLOCK AND PREPARATION METHOD THEREOF

CROSS REFERENCE TO THE RELATED APPLICATIONS

This application is the national phase entry of International Application No. PCT/CN2018/000201, filed on May 31, 2018, which is based upon and claims priority to Chinese Patent Application No. 201810088477.8, filed on Jan. 30, 2018, the entire contents of which are incorporated herein by reference.

TECHNICAL FIELD

The present invention relates to an instant dosage form of gel product, and in particular to a gel product instant-dissolving block and a preparation method thereof.

BACKGROUND

The gel is a solid block-shaped orally-administrated formulation prepared by decocting animal skins, bones, armors or horns with water to obtain a colloid, carrying out concentrating to obtain a condensed colloid and then drying the condensed colloid, which is a conventional formulation form of the gel traditional Chinese medicine such as donkey-hide gelatin, tortoise shell gel, antler gel and the like, and has long history. The conventional gel has a hard block shape, and needs to be smashed and melted by heat with rice wine for 24 hours or more when administrated or to be powdered by a chalking machine for infusion, which requires long processing time or special grinding equipment, resulting in complexity in the administration and causing many inconveniences.

Compared with a powder product, the block-shaped product has many advantages such as small size, convenience for carrying, difficulty in pouring out, and no flying of fine powder or residues in the bag. However, the moldability and instant solubility of the block-shaped product are contradictory, that is, the product can be molded by being compressed under high pressure but the solubility of such a product is poor; on the other hand, the solubility can be improved when the pressure is lowered, but sufficient hardness cannot be formed and the moldability is poor, which cannot meet the needs of packaging and transportation. In the industry for gel products, the conventional products are ordinary oral tablets, buccal tablets, dispersible tablets, or chewable tablets prepared by compression under a relatively high pressure, and require addition of various chemical tableting auxiliary materials, thereby having relatively low purity or being unable to achieve the instant dissolution for infusion. The conventional technical solution for instant dissolution of block/sheet-like products is an effervesce technique, wherein the material is mixed with citric acid and sodium bicarbonate and then is compressed, and generates a large amount of carbon dioxide through acid-base reaction with water to accelerate disintegration, thereby achieving the purpose of instant dissolution. Since the effervescent tablet needs to add a large amount of chemical auxiliary materials, the product has low purity, and the acidity of the solution after dissolution is high, leading to the loss in the original mouthfeel of the gel product.

SUMMARY

In order to solve the problem that a block-shaped gel product is not easy to dissolve, the present invention provides a gel product instant-dissolving block and a preparation method thereof, which can be rapidly dissolved without adding any chemical disintegrants or cosolvents, to achieve increase the convenience of carrying, using and administering the gel product.

In order to solve the above problem, the present invention provides the following technical solutions.

A method for preparing a gel product instant-dissolving block, comprising:

(1) adding water into a raw material gel to dissolve the raw material gel and carrying out concentrating to obtain a gel solution;

(2) carrying out a vacuum belt drying treatment on the gel solution to obtain a cellular gel body;

(3) grinding the gel body and carrying out screening to obtain sheet-like gel powder with a particle size being equal to or larger than 80 meshes; and (4) moistening the gel powder with 85 to 95% ethanol, and directly carrying out compressing on moistened material which is not dried at a compression ratio of 30 to 60%, thereby obtaining the gel product instant-dissolving block.

As a preferred technical solution of the present invention, a relative density of the gel solution is 1.16 to 1.19 (75° C.).

As a preferred technical solution of the present invention, a vacuum degree of the vacuum belt drying is 98 to 99 KPa, a drying temperature is 90 to 102° C., and a running speed of a drying belt is 16 to 18 cm/min.

As a preferred technical solution of the present invention, the grinding is carried out by a grinder, a rotating speed of the grinder is 10 to 15 Hz, and an aperture of a grinding screen is 2 to 3 mm.

As a preferred technical solution of the present invention, an amount of the ethanol to be added is 10% to 30% of the mass of the gel powder.

As a preferred technical solution of the present invention, further comprising: (5) carrying out second moistening on a surface of the compressed block with ethanol after the compression in step (4), and then carrying out drying to obtain a gel product instant-dissolving block.

As a further preferred technical solution of the present invention, an amount of ethanol to be used in step (5) is 1% to 5% of the weight of the compressed block.

As a further preferred technical solution of the present invention, in step (5), the drying is to dry the moistened compressed block until water content of the compressed block is ≤10%, that is, the gel product instant-dissolving block is obtained.

As a preferred technical solution of the present invention, crystal sugar and/or rice wine are further added when the raw material gel is dissolved.

The present invention further provides a gel product instant-dissolving block prepared by the above technical solution, wherein the gel product instant-dissolving block has a loose pore structure and a density of 0.4 to 0.8 g/cm$^3$.

As a preferred technical solution of the present invention, the gel product instant-dissolving block has a hardness being greater than 1.5 kg, a crisp texture, and a crystalline luster.

Compared with the prior art, the present invention has the following beneficial effects.

The present invention provides a gel product instant-dissolving block and a preparation method thereof, which comprises the following steps: adding water into a raw material gel to dissolve the raw material gel and carrying out concentrating to obtain a gel solution; carrying out a vacuum belt drying treatment on the gel solution to obtain a cellular gel body; grinding the gel body and carrying out screening to obtain gel powder with a particle size being equal to or larger than 80 meshes; and moistening the gel powder with 85 to 95% ethanol, and carrying out compression at a compression ratio of 30 to 60% to obtain a block. The present invention adopts a vacuum belt drying process to prepare powders, controls the particle size of the sheet-like gel powder to eliminate a granulation process of conventional tableting, and carries out an optimal control on the moistening process according to the characteristics of the material to ensure the fluidity and compressing performance of the material. By the combined effects of the steps including obtaining cellular gel body through the vacuum belt drying, grinding at a controlled particle size, carrying out the moistening process, and compressing at low compression ratio, the present invention achieves the loose pore structure of the finished product, and effectively solves the technical problem that the block-shaped gel product cannot be rapidly dissolved.

The present invention uses the vacuum belt drying process to dry the gel solution to obtain an irregular cellular gel body. Since the gel solution is directly dried under a high vacuum degree, a large number of bubbles are formed during the drying process of the gel solution, and the gel solution after drying can form the cellular gel body under a certain relative density. After grinding to the required particle size range at a low speed, irregular sheet-like gel powder is formed. The gel powder has good fluidity and good appearance. Since the irregular sheet-like gel powders support each other, it is possible to form a microscopically loose pore structure at a very low compression ratio, and the moisture can quickly penetrate into the product through the pores at the time of dissolution to accelerate the dissolution of the product, and in this way, the compressed block-shaped gel product has excellent instant solubility.

The present invention breaks through the technical bottleneck of the contradiction between the moldability and the instant solubility of the block-shaped gel product. The gel product instant-dissolving block of the present invention has a solid texture and high hardness (tested with a texture analyzer, the hardness of the product is >1.5 kg), which can meet the requirements of packaging and transportation while maintaining the block shape of conventional gel. At the same time, the gel product instant-dissolving block of the present invention has a pore structure inside, a high superficial area/volume ratio, and a low product density which is within the range of 0.4 to 0.8 g/cm$^3$, and can rapidly dissolve within 2 min in hot water above 95° C. without being ground or being melted with hot water for a long time.

The gel product instant-dissolving block of the present invention has a special texture and can be administrated in multiple ways. The product is solid the appearance but crisp in the texture, and thus, can be buccally administrated or directly chewed, in addition to infusion with hot water or the use in soup, thereby meeting consumers' demand for administration in different situations.

Compared with traditional donkey-hide gelatin powder, the gel product instant-dissolving block of the present invention has a special glittering luster, a novel feeling in the appearance, and meets consumers' demand for unique appearances of the product.

DETAILED DESCRIPTION OF THE EMBODIMENTS

Figure 1:
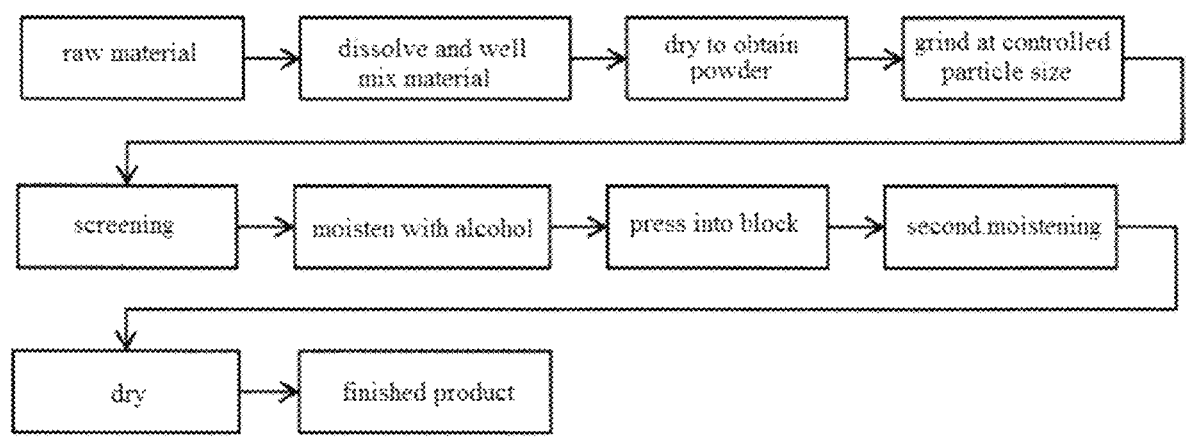
FIG. 1 is a flowchart of a method for preparing a gel product instant-dissolving block in an embodiment of the present invention.

In order to overcome the technical problems of a conventional block-shaped gel product such as poor solubility, inconvenience in use, and single administration method of the same product, the present invention provides a method of preparing a gel product instant-dissolving block, comprising:

(1) adding water into a raw material gel to dissolve the raw material gel and carrying out concentrating to obtain a gel solution;

(2) carrying out a vacuum belt drying treatment on the gel solution to obtain a cellular gel body;

(3) grinding the gel body and carrying out screening to obtain gel powder with a particle size being equal to or larger than 80 meshes; and (4) moistening the gel powder with 85 to 95% ethanol, and carrying out compression at a compression ratio of 30 to 60%, thereby obtaining the gel product instant-dissolving block.

In the present invention, the raw material gel is a well-known homology gel for medicine and food or a raw material of the gel traditional Chinese medicine, such as donkey-hide gelatin, tortoise shell gel, staghorn gel, yellow gelatin and other gel products. In the present invention, there is no particular limitation on the kind of raw material gel, and all of the above-mentioned kinds of raw material gels may be applied to the present invention.

The water is added to the raw material gel to dissolve it. The method of dissolving the raw material gel is not particularly limited in the present invention, and a conventional method for dissolving the raw material gel in this technical filed may be used, such as heat dissolution. Preferably, in the present invention, the raw material gel is mixed with the water of 3 to 5 times the mass of the raw material gel, and then heated and stirred to completely dissolve. The conventional operations of those skilled in the art may be adopted for the heating temperature and the heating time. Preferably, in the present invention, crystal sugar and/or rice wine are added during the dissolution process of the raw material gel to adjust the taste of the gel product instant-dissolving block.

The dissolved raw material gel is concentrated to obtain the gel solution. The concentration method is not particularly limited in the present invention, and a conventional concentration method in this technical filed may be used, such as heat concentration. In the present invention, the relative density of the gel solution after concentration is preferably 1.16 to 1.19 (75° C.). When the relative density after the concentration is too low, the gel solution is too thin, and may flow out from the drying belt during the vacuum belt drying process, resulting in the loss; contrarily, when the relative density is too high, it is impossible to form the cellular gel body during the vacuum belt drying process, or the thickness of the gel body sheet becomes too high, which affects the drying effect and the instant solubility of the finished product. The gel product of the present invention has the most suitable viscosity and the best drying effect within this relative density range.

The present invention adopts the vacuum belt drying method to process the gel solution to obtain the irregular cellular gel body. The parameters of the vacuum belt drying preferably include that, the vacuum degree is preferably 98 to 99 KPa, more preferably 98 KPa; the drying temperature is preferably 90 to 102° C., more preferably 95 to 97° C.; and the running speed of the drying belt is 16 to 18 cm/min, more preferably 17 cm/min.

A belt drier may be used when the gel solution is dried by the vacuum belt drying method in the present invention. Specifically, the gel solution is directly conveyed to the inside of the vacuum belt drier via a conveying mechanism, and is then spread on the drying belt in the drier to be dried. In the present invention, the feeding temperature of the gel solution is preferably 50 to 70° C., more preferably 56 to 67° C.; the feeding rate of the gel solution is preferably 10 to 20 L/h, more preferably 14 to 18 L/h; and the gel solution is dried by being heated on the drying belt by a heat source. In the present invention, the drying temperature is preferably divided into five stages, which are 95±5° C., 97±5° C., 97±5° C., 97±5° C., 25±5° C. in order; and the last stage is to restore the temperature of the dried gel body to room temperature. After the gel body material is already dried and cooled, the dried gel body is peeled off from the drying belt, and the dried gel body is cut off by a guillotine device that moves up and down. In the present invention, the movement frequency of the guillotine device is preferably 15 to 25 seconds/time, more preferably 18 to 22 seconds/time, and a sheet-like gel body in the form of coarse powder is obtained. In the present invention, the water content of the dried gel body is preferably 2% to 6%, more preferably 3 to 5%. The thickness of the prepared sheet-like gel body is preferably 0.3 mm, which is more conducive to accelerating the dissolution of the compressed gel product.

Figure 4:
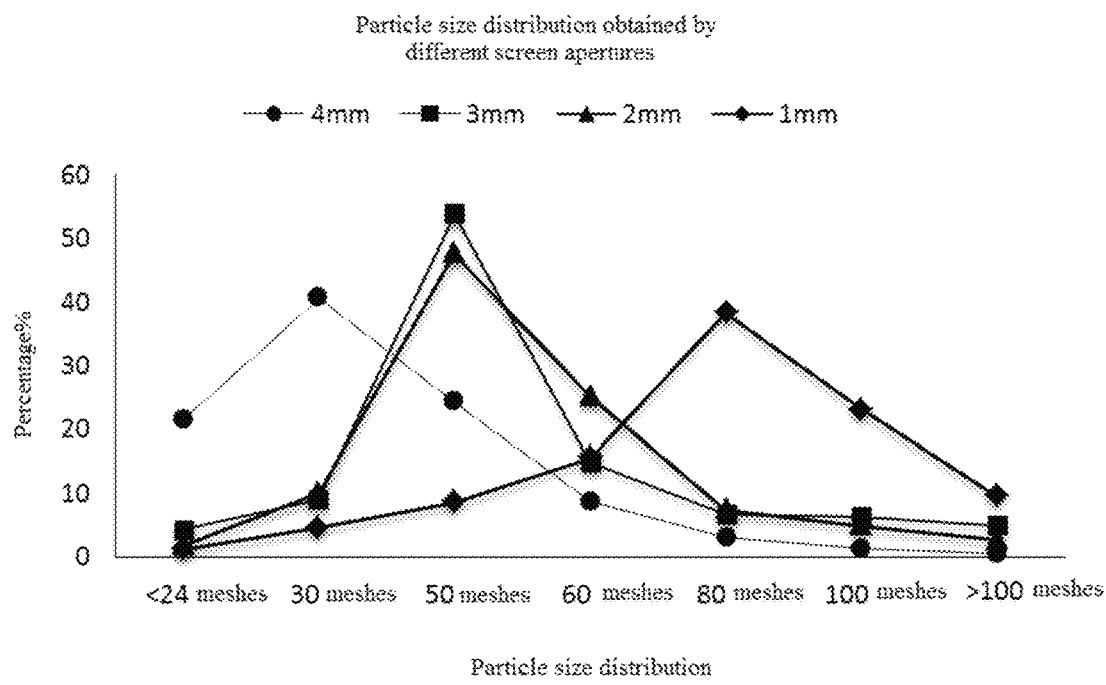
FIG. 4 shows a particle size distribution under different mesh aperture grinding conditions.

In the present invention, the sheet-like gel body is ground. The grinding method is not particularly limited in the present invention, and a conventional grinding method in the technical field may be used. A grinder is preferably used for grinding in the present invention, and the frequency of the grinder is preferably 10 to 15 Hz, and more preferably 12 to 14 Hz, which is low-speed grinding. In the present invention, the aperture of the grinding screen is preferably 2 to 3 mm. The present invention conducts grinding experiments under 15 Hz by respectively adopting screens with apertures of 1, 2, 3, and 4 mm, and detects particle size distribution of the ground material powder. As shown in FIG. 4, the results show that the distribution ratios within the rage of 30 to 80 meshes are the highest when the screen apertures are 2 mm and 3 mm, which are 84.4% and 90.42%, respectively, and the particle size is suitable. After the sheet-like gel body is compressed into a block, the formed compressed block easily forms a certain quantity of pores with a certain size, since the gel powder has a sheet-like structure and the compression pressure is extremely small.

The ground materials are screened to obtain the gel powder with a particle size being equal to or larger than 80 meshes. In the present invention, the particle size of the gel powder is preferably 30 to 80 meshes, and more preferably 40 to 70 meshes. In the present invention, a shaking screen corresponding to the screening size is preferably used for screening, and the obtained gel powder after screening are used for compressing into blocks. The gel powder obtained by grinding and screening under the above conditions in the present invention preferably has a bulk density of 0.4 to 0.6 g/ml, a tap density of 0.5 to 0.7 g/ml, an angle of repose of 35 to 45°, and has a good fluidity and is easy to post-compress. If the gel powder is too fine, the compressed block may have too small pore, high density and poor solubility; contrarily, if the gel powder is too large, the fillers may be uneven during tableting, resulting in poor weight uniformity of the finished product. Therefore, the gel powder with the above-mentioned particle size of the present invention is compressed into a block, which can not only solve the problem of solubility, but also ensure the quality of the compressed block.

After the gel powder is obtained, the present invention uses the ethanol as a moistening agent to uniformly moisten the gel powder. The viscosity of the gel powder is increased by moderate moistening, and thus, the gel powder can be compressed and molded at a relatively low compression ratio to form a block with the loose pore structure; and in this way, the product has excellent instant solubility. In the present invention, it is preferred that the ethanol is uniformly added into the gel powder by spraying, and that the stirring is carried out during the addition to ensure the moistening uniformity. In the present invention, the volume concentration of the ethanol is 85 to 95%, more preferably 90 to 95%. If the ethanol concentration is too low, the gel powder is easy to agglomerate, and cannot be filled and compressed; contrarily, if the ethanol concentration is too high, the viscosity is insufficient for compression molding. In the present invention, the amount of the ethanol to be added is preferably 10% to 30% of the mass of the gel powder, and more preferably 15 to 26%, at which the gel powder is moist enough for compression molding.

The moistened gel powder is compressed into block. The compression method is not particularly limited in the present invention, and a conventional compression method in the technical field may be used. In the present invention, the compression ratio of the compressing is 30 to 60%, more preferably 40 to 50%. The compression ratio of the present invention=(thickness before compressing−thickness after compressing)/thickness before compressing). Under this compression ratio, the moldability of the compressed block is good enough to meet the needs of packaging and transportation, and the dissolution rate in 95° C. hot water can also be maintained at about 92 to 100 s; and thus, the instant solubility and moldability have a good balance. After being compressed into a block, the gel product instant-dissolving block of the present invention is obtained.

As a preferred embodiment, in the present invention, the surface of the compressed block is subjected to second moistening with the ethanol to further dissolve and bind fine powders on the surface layer, which solves the problem that powders easily fall off from the product surface. In the present invention, the amount of the ethanol is preferably 1 to 5% of the mass of the compressed block, and more preferably 2 to 4% thereof. The volume concentration of the ethanol for second moistening is preferably 85 to 95%, and more preferably 93 to 95%.

The moistened compressed block is dried to obtain the gel product instant-dissolving block of the present invention. Because the moistened gel powder is directly compressed without being dried in the present invention, the compressed block still contains relatively high water content, and when directly dried at high temperature, the gel powder is dissolved at the high temperature and internal compaction occurs, which seriously affect the instant dissolubility of the product. The drying in the present invention is preferably performed by first leaving the moistened compressed block at a relatively low temperature of room temperature such that the water can slowly evaporate with the ethanol without causing the dissolution and compaction of the gel powder. In the present invention, it is preferable to leave the moistened compressed block at room temperature for 30 minutes or more, more preferably to leave it for 40 to 60 minutes, and then dry it. The drying method is not particularly limited in the present invention, and a conventional drying method in the technical field may be used, such as drying at room temperature, heating and drying or decompression drying. The compressed block after second moistening is dried until the water content of the compressed block is ≤10% to obtain the gel product instant-dissolving block. If the heating and drying are adopted, in the present invention, the compressed block is preferably first dried at 40 to 60° C. for 30 to 60 min, and then dried at 90 to 105° C. until the water content of the compressed block is ≤10%. Through experiments, the drying first at a temperature of 40 to 60° C. does not cause the dissolution and compaction in the gel block, but can accelerate the drying speed; and the final drying under the condition of 90 to 105° C. can accelerate the drying speed and has a certain sterilization effect. If the decompression drying is adopted, the compressed block is preferably decompression dried under the condition of 40 to 60° C. until the water content of the compressed block is ≤10%.

The present invention further provides the gel product instant-dissolving block prepared by the above technical solution. The gel product instant-dissolving block has a pore structure and a density of 0.4 to 0.8 g/cm$^3$, and can quickly dissolve in hot water within 2 minutes above 95° C., without being ground or being melted by heat for a long time, thereby achieving good instant dissolubility.

The gel product instant-dissolving block of the present invention has a solid texture and a high hardness, and the hardness of the product tested by a texture analyzer is >1.5 kg, which can meet the requirements of packaging and transportation while maintaining the block shape of conventional gel. The gel product instant-dissolving block of the present invention is solid in the appearance but crisp in the texture, and thus, can be buccally administrated or directly chewed, in addition to infusion with hot water or the use in soup, thereby meeting consumers' demand for administration in different situations.

In order to make the objectives, technical solutions and advantages of the present invention clearer, the present invention will be described in detail below in conjunction with the embodiments, which are not intended to limit the protection scope of the present invention.

Embodiment 1

(1) Adding the donkey-hide gelatin raw material together with a certain amount of crystal sugar and rice wine to the water of 5 times the total mass, and then carrying out heating and stirring to completely dissolve them. Concentrating the dissolved donkey-hide gelatin solution to a relative density of 1.16 to 1.19 (75° C.);

(2) Carrying out the drying treatment on the concentrated donkey-hide gelatin solution by the vacuum belt drying process to obtain coarse powder. The parameters for the vacuum belt drying include a feeding temperature of 67° C., a feeding speed of 19 L/h, a running speed of the crawler of 15 cm/min; the first, second, third, fourth and fifth stages of the heating temperature of 95±5° C., 97±5° C., 97±5° C., 97±5° C., 25±5° C., respectively; a cutter of 25 seconds/time, and a vacuum degree of 98 KPa.

(3) Grinding with controlled particle size: grinding the coarse powder obtained by drying with a low-speed grinder at a frequency of 15 Hz and a screen having an aperture of 2 to 3 mm. Carrying out screening with 30 meshes to 80 meshes shaking screen, and selecting the particle between 30 meshes to 80 meshes as the donkey-hide gelatin powder, and setting aside.

(4) Uniformly adding ethanol of 95% volume concentration as a moistening agent into the donkey-hide gelatin powder by spraying, carrying out stirring during addition to ensure the moistening uniformity. The amount of ethanol to be added is 15% of the amount of donkey-hide gelatin powder.

(5) Compressing the moistened donkey-hide gelatin powder into block with a briquetting press at a compression ratio of 50%.

(6) Carrying out second moistening on the surface of the compressed donkey-hide gelatin block with the ethanol of 95% volume concentration, wherein the amount of the ethanol to be used is 5% of the mass of the donkey-hide gelatin block.

(7) Leaving the moistened instant donkey-hide gelatin block at room temperature for 30 minutes, then drying it in an oven at 60° C. for 60 minutes and then at 100° C. until the water content ≤10%, and in this way, the instant donkey-hide gelatin block of the present invention can be obtained.

Figure 2A:
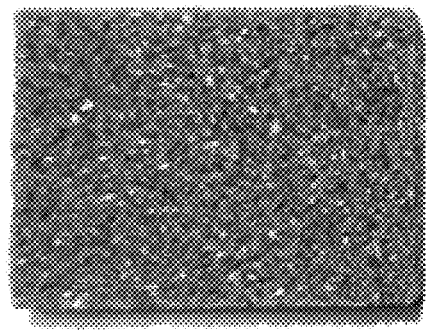
FIG. 2A shows an instant donkey-hide gelatin block of Embodiment 1 of the present invention and FIG. 2B shows a donkey-hide gelatin block obtained by conventional process.
Figure 3:
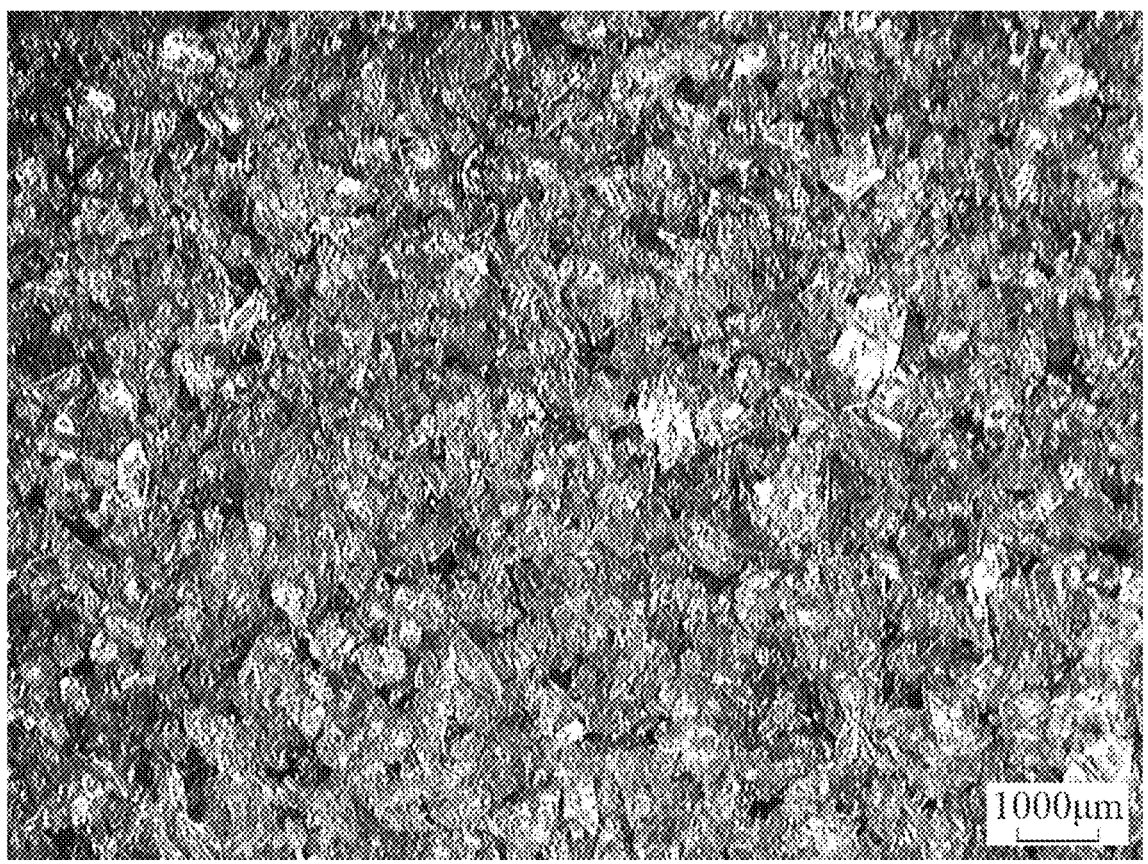
FIG. 3 is a 10-times enlarged view of the instant donkey-hide gelatin block of Embodiment 1 of the present invention.

FIG. 2A shows the instant donkey-hide gelatin block prepared in Embodiment 1 of the present invention, and FIG. 3 is a 10-times enlarged view of the instant donkey-hide gelatin block. It can be clearly seen that there are a large number of pore structures in the instant donkey-hide gelatin block. The hardness of the instant donkey-hide gelatin block which is tested by the texture analyzer is 6.3 Kg, the density of the instant donkey-hide gelatin block is 0.73 g/cm$^3$, and the maximum block weight deviation is 2%.

Embodiment 2

(1) Adding the tortoise shell raw material together with crystal sugar to the water of 3 times the total mass, and then carrying out heating and stirring to completely dissolve them. Concentrating the dissolved gel solution to a relative density of 1.16 to 1.19 (75° C.);

(2) Carrying out the drying treatment on the concentrated tortoise shell gel solution by the vacuum belt drying process to obtain coarse powder. The parameters for the vacuum belt drying include a feeding temperature of 62° C., a feeding speed of 14 L/h, a running speed of the crawler of 13 cm/min; the first, second, third, fourth and fifth stages of the heating temperature of 95±5° C., 97±5° C., 97±5° C., 97±5° C., 25±5° C., respectively; a cutter of 19 seconds/time, and a vacuum degree of 98 KPa.

(3) Grinding with controlled particle size: grinding the coarse powder obtained by drying with a low-speed grinder at a frequency of 13 Hz and a screen having an aperture of 2 to 3 mm. Carrying out screening with 30 meshes to 80 meshes shaking screen, and selecting the particle between 30 meshes to 80 meshes as the tortoise shell gel powder, and setting aside.

(4) Uniformly adding ethanol of 90% volume concentration as a moistening agent into the tortoise shell gel powder by spraying, carrying out stirring during addition to ensure the moistening uniformity. The amount of ethanol to be added is 23% of the amount of tortoise shell gel powder.

(5) Compressing the moistened tortoise shell gel powder into block with a briquetting press at a compression ratio of 50%.

(6) Carrying out second moistening on the surface of the compressed tortoise shell gel block with the ethanol of 95% volume concentration, wherein the amount of the ethanol to be used is 5% of the mass of the gel block.

(7) Leaving the moistened tortoise shell gel block at room temperature for 40 minutes, then drying it in an oven at 48° C. for 52 minutes and then at 93° C. until the water content and in this way, the instant tortoise shell gel block of the present invention can be obtained.

The hardness of the instant tortoise shell gel block which is tested by the texture analyzer is 5.3 Kg, and the density of the instant tortoise shell block is 0.69 g/cm$^3$.

Embodiment 3

(1) Adding the antler gel block together with rice wine to the water of 4 times the total mass, and then carrying out heating and stirring to completely dissolve them. Concentrating the dissolved antler gel solution to a relative density of 1.16 to 1.18 (75° C.);

(2) Carrying out the drying treatment on the concentrated antler gel solution by the vacuum belt drying process to obtain coarse powder. The parameters for the vacuum belt drying include a feeding temperature of 50° C., a feeding speed of 10 L/h, a running speed of the crawler of 10 cm/min; the first, second, third, fourth and fifth stages of the heating temperature of 95±5° C., 97±5° C., 97±5° C., 97±5° C., 25±5° C., respectively; a cutter of 15 seconds/time, and a vacuum degree of 99 KPa.

(3) Grinding with controlled particle size: grinding the coarse powder obtained by drying with a low-speed grinder at a frequency of 10 Hz and a screen having an aperture of 2 to 3 mm. Carrying out screening with 30 meshes to 80 meshes shaking screen, and selecting the particle between 30 meshes to 80 meshes as the antler gel powder, and setting aside.

(4) Uniformly adding ethanol of 88% volume concentration as a moistening agent into the antler gel powder by spraying, carrying out stirring during addition to ensure the moistening uniformity. The amount of ethanol to be added is 12% of the amount of antler gel powder.

(5) Compressing the moistened antler gel powder into block with a briquetting press at a compression ratio of 45%.

(6) Carrying out second moistening on the surface of the compressed antler gel block with the ethanol of 95% volume concentration, wherein the amount of the ethanol to be used is 5% of the mass of the antler gel block.

(7) Leaving the moistened antler gel block at room temperature for 50 minutes, then drying it by the decompression drying method at 40 to 60° C. until the water content and in this way, the instant antler gel block of the present invention can be obtained.

The hardness of the instant antler gel block which is tested by the texture analyzer is 4.8 Kg, and the density of the instant antler gel block is 0.65 g/cm$^3$.

Embodiment 4

(1) Adding the donkey-hide gelatin raw material together into the water of 5 times the total mass, and then carrying out heating and stirring to completely dissolve it. Concentrating the dissolved donkey-hide gelatin solution to a relative density of 1.16 to 1.19 (75° C.);

(2) Carrying out the drying treatment on the concentrated donkey-hide gelatin solution by the vacuum belt drying process to obtain coarse powder. The parameters for the vacuum belt drying include a feeding temperature of 67° C., a feeding speed of 19 L/h, a running speed of the crawler of 15 cm/min; the first, second, third, fourth and fifth stages of the heating temperature of 95±5° C., 97±5° C., 97±5° C., 97±5° C., 25±5° C., respectively; a cutter of 25 seconds/time, and a vacuum degree of 98 KPa.

(3) Grinding with controlled particle size: grinding the coarse powder obtained by drying with a low-speed grinder at a frequency of 15 Hz and a screen having an aperture of 4 mm. Carrying out screening with 10 meshes to 20 meshes shaking screen, and selecting the particle between 10 meshes to 20 meshes as the donkey-hide gelatin powder, and setting aside.

(4) Uniformly adding ethanol of 95% volume concentration as a moistening agent into the donkey-hide gelatin powder by spraying, carrying out stirring during addition to ensure the moistening uniformity. The amount of ethanol to be added is 15% of the amount of donkey-hide gelatin powder.

(5) Compressing the moistened donkey-hide gelatin powder into block with a briquetting press at a compression ratio of 50%.

(6) Carrying out second moistening on the surface of the compressed donkey-hide gelatin block with the ethanol of 95% volume concentration, wherein the amount of the ethanol to be used is 5% of the mass of the donkey-hide gelatin block.

(7) Leaving the moistened instant donkey-hide gelatin block at room temperature for 30 minutes, then drying it in an oven at 60° C. for 60 minutes and then at 100° C. until the water content 10%, and in this way, the instant donkey-hide gelatin block of the present invention can be obtained.

The hardness of the instant donkey-hide gelatin block which is tested by the texture analyzer is 1.6 Kg, the density of the instant donkey-hide gelatin block is 0.52 g/cm$^3$, and the maximum block weight deviation is 8%.

Comparative Example 1

The other steps are the same as in Embodiment 1 except that the particle size of the donkey-hide gelatin powder in step (3) is 100 to 150 meshes.

The hardness of the prepared instant donkey-hide gelatin block is 7.3 Kg, and the density of the instant donkey-hide gelatin block is 1.2 g/cm$^3$. Since the particle size is too fine, the material gap is small and the filling content is high, the compressed product has high density, high hardness and small pores under the same conditions. As a result, the instant solubility is poor, and the dissolution time is 5 minutes.

Comparative Example 2

The other steps are the same as in Embodiment 1 except that the volume concentration of ethanol in step (4) is 84%.

When the ethanol concentration is less than 85%, after the ethanol is added, the material powder will immediately form a large-particle hard mass due to the high-water content, the uniformity and the fluidity of the material become poor, and the material cannot be compressed.

Comparative Example 3

The conventional method for compressing the donkey-hide gelatin block includes the following steps: carrying out compressing using the donkey-hide gelatin as the main raw material after added with appropriate amount of auxiliary materials such as magnesium stearate and microcrystalline cellulose. The donkey-hide gelatin is ground to fine powder of equal to or larger than 80 meshes, or spray-dried to obtain fine powder of equal to or larger than 80 meshes; the fine powder of donkey-hide gelatin and the auxiliary materials such as magnesium stearate and microcrystalline cellulose are subjected to a dry granulation process or a moistened granulation process to obtain dry granules with the water content of less than 5%, and the granules are granulated and compressed into block.

Figure 2B:
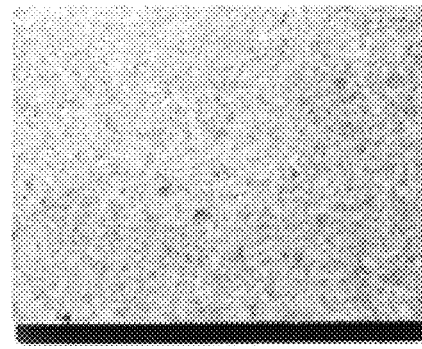

FIG. 2B is the conventional donkey-hide gelatin compressed block. Compared with the instant donkey-hide gelatin block in FIG. 2A, since the raw material powder of the conventional donkey-hide gelatin block is fine and compact, the density of the prepared donkey-hide gelatin block is 1.6 g/cm$^3$, the solubility is poor, and the dissolution time reaches 78 min, which are unable to achieve the effect of rapid dissolution.

The dissolution experiment includes the following steps:

Placing the donkey-hide gelatin blocks prepared in Embodiment 1, Embodiment 4 and Comparative Examples 1 to 3, and the conventional donkey-hide gelatin block in 100 mL of 95° C. hot water, and starting counting from the time when the samples are put into cups, and the time until the samples completely visually collapse and dissolve is the dissolution time, see the table below.

| Sample | Dissolution time | Remarks |
| --- | --- | --- |
| Embodiment 1 | 1'40" | maximum block weight deviation of 2% |
| Embodiment 4 | 1'10" | maximum block weight deviation of 8% |
| Comparative Example 1 | 5'08" | — |
| Comparative Example 2 | — | Material agglomerate, uncontrollable |
| Comparative Example 3 | 78'10" | — |
| Conventional donkey-hide gelatin block (gel) | 13.5 h | — |

The method for testing the hardness of the product comprises the following steps:

Placing the sample to be tested in the center of a test board to test the sample with a three-point bending probe, wherein the sample to be tested has a width of 32 mm, a fulcrum spacing of 20 mm, a method mode of Compression, a trigger force of 5.0 g, a pre-test speed of 10.00 mm/s, and a test speed of 1.00 mm/s, the hardness value of the product is the maximum force value during the three-point bending test. The unit of hardness is expressed in kg.

Merely preferred embodiments of the present application are described above. It should be noted that, all modifications and changes made by those skilled in the art without departing from the spirit of the present invention, shall fall within the protection scope of the present invention.

What is claimed is:

1. A method for preparing a gel product instant-dissolving block, comprising the following steps:
    (1) adding water into a raw material gel to dissolve the raw material gel to obtain a dissolved gel solution, and concentrating the dissolved gel solution to obtain a gel solution;
    (2) carrying out a vacuum belt drying treatment on the gel solution to obtain a cellular gel body;
    (3) grinding the cellular gel body and carrying out a screening on the cellular gel body to obtain gel powder with particles having a particle size of 30 to 80 mesh; and
    (4) moistening the gel powder with 85-95% ethanol to obtain moistened gel powder, wherein in the 85-95% ethanol, a volume concentration of ethanol is 85-95%, and a balance is water, and wherein an amount of the 85-95% ethanol is 10% to 30% of a mass of the gel powder, and forming the gel product instant-dissolving block;
    wherein a vacuum degree of the vacuum belt drying treatment is 98 to 99 KPa, a drying temperature of the vacuum belt drying treatment is 90 to 102° C., and a running speed of a drying belt of the vacuum belt drying treatment is 16 to 18 cm/min.

2. The method according to claim 1, wherein a relative density of the gel solution to the dissolved gel solution is 1.16 to 1.19; and the relative density of the gel solution is measured at 75° C.

3. The method according to claim 1, wherein the grinding is carried out by a grinder, a rotating speed of the grinder is 10 to 15 Hz, and an aperture size of a grinding screen of the grinder is 2 to 3 mm.

4. The method according to claim 1, further comprising:
    (5) carrying out a second moistening on a surface of the gel product instant-dissolving block with the 85-95% ethanol after step (4) to obtain a moistened block, and then carrying out a drying on the moistened block to obtain a final product of the gel product instant-dissolving block.

5. The method according to claim 4, wherein an amount of the 85-95% ethanol in step (5) is 1% to 5% of a weight of the gel product instant-dissolving block.

6. The method according to claim 5, wherein in step (5), the drying is to dry the moistened block until a water content of the moistened block is less than or equal to 10%.

7. The method according to claim 1, wherein in step (1), a crystal sugar, a rice wine, or a combination thereof is added to the raw material gel when the raw material gel is dissolved.

8. The method according to claim 2, wherein in step (1), a crystal sugar, a rice wine, or a combination thereof is added to the raw material gel when the raw material gel is dissolved.

9. The method according to claim 3, wherein in step (1), a crystal sugar, a rice wine, or a combination thereof is added to the raw material gel when the raw material gel is dissolved.

10. The method according to claim 4, wherein in step (1), a crystal sugar, a rice wine, or a combination thereof is added to the raw material gel when the raw material gel is dissolved.

11. The method according to claim 5, wherein in step (1), a crystal sugar, a rice wine, or a combination thereof is added to the raw material gel when the raw material gel is dissolved.

12. The method according to claim 6, wherein in step (1), a crystal sugar, a rice wine, or a combination thereof is added to the raw material gel when the raw material gel is dissolved.

* * * * *